United States Patent [19]

Fukuyama

[11] 3,969,822

[45] July 20, 1976

[54] POROUS, STATIC PRESSURE AIR BEARING DEVICE IN A DENTIST'S HANDPIECE

[75] Inventor: Hiromasa Fukuyama, Fujisawa, Japan

[73] Assignee: Nippon Seiko Kabushiki Kaisha, Tokyo, Japan

[22] Filed: Mar. 1, 1974

[21] Appl. No.: 447,208

[30] Foreign Application Priority Data

Mar. 6, 1973 Japan .......................... 48-27291[U]

[52] U.S. Cl. .................................................. 32/27
[51] Int. Cl.² ........................................... A61C 1/10
[58] Field of Search ................. 32/26, 27; 415/503, 415/112; 308/DIG. 1, 5 R, 9, 174

[56] References Cited
UNITED STATES PATENTS

| | | |
|---|---|---|
| 2,442,202 | 5/1948 | Hughes-Caley ..................... 415/112 |
| 2,645,534 | 7/1953 | Becker ............................... 415/112 |
| 3,268,205 | 8/1966 | Allen et al. ...................... 415/503 X |
| 3,384,344 | 5/1968 | Ota ................................. 415/503 X |
| 3,426,429 | 2/1969 | Hoffmeister et al. ........... 415/503 X |
| 3,451,134 | 6/1969 | Erickson et al. ................. 415/503 X |
| 3,471,125 | 10/1969 | Taubald et al. ..................... 415/503 |
| 3,475,065 | 10/1969 | Weichsel ............................ 308/5 R |
| 3,589,828 | 6/1971 | Mosimann .......................... 32/27 X |
| 3,639,074 | 2/1972 | Killick ............................. 415/503 X |

Primary Examiner—Robert Peshock
Assistant Examiner—Jack Q. Lever
Attorney, Agent, or Firm—Shapiro and Shapiro

[57] ABSTRACT

In a dentist's handpiece, a porous, static pressure air bearing device includes a rotatable shaft for mounting thereon a cutting tool, a bearing case, an air bearing portion provided in the bearing case for supporting the rotatable shaft, and a turbine blade formed integrally with the shaft or mounted on the shaft. The air bearing portion is formed of porous material.

7 Claims, 1 Drawing Figure

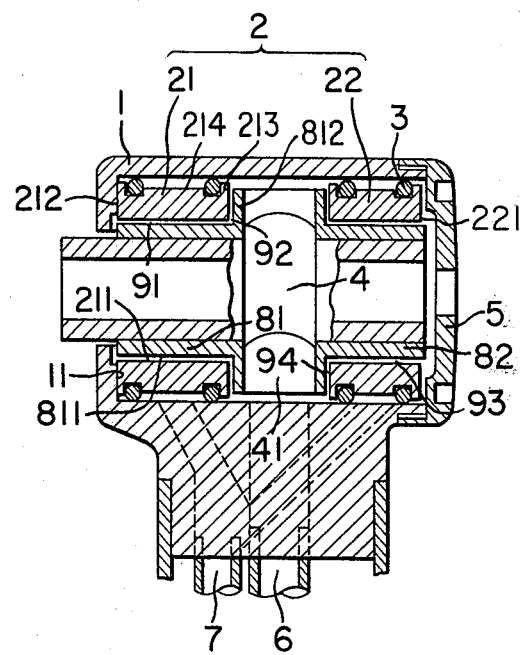

POROUS, STATIC PRESSURE AIR BEARING DEVICE IN A DENTIST'S HANDPIECE

BACKGROUND OF THE INVENTION

1. Field of the Invention

This invention relates to a porous, static pressure air bearing device in a dentist's handpiece.

2. Description of the Prior Art

In the dentist's handpiece of the type using the conventional air bearing, the air bearing portion employed therein has taken the form of an air bearing wherein a number of fine apertures of the orifice type or of the inherently compensated type are formed in the bearing portion. These types of bearings have suffered from two disadvantages. One of them is that forming a number of fine apertures in the bearing portion is considerably difficult and inefficient. The other disadvantage is that the thrust load capacity is relatively low because the thrust bearing taking the load in the thrust direction of the rotatable shaft is formed by air leaving the radial bearing section.

SUMMARY OF THE INVENTION

It is an object of the present invention to eliminate the above-noted disadvantages and to provide a porous, static pressure air bearing device in a dentist's handpiece wherein the air bearing portion is formed of porous material to increase the ease of working and the thrust load capacity.

In a preferred form of the present invention, the porous, static pressure air bearing device in a dentist's handpiece comprises a rotatable shaft for mounting thereon a cutting tool, a bearing case, an air bearing portion provided in the bearing case for supporting the rotatable shaft, and a turbine blade formed integrally with the rotatable shaft or mounted on the rotatable shaft. The air bearing portion may be formed of either porous material such as sintered metal or ceramics or porous synthetic resin.

The invention will become more fully apparent from the following detailed description of a preferred embodiment thereof taken in conjunction with the accompanying drawing.

BRIEF DESCRIPTION OF THE DRAWING

The FIGURE of the drawing is a front view, partly in cross section, of the device according to an embodiment of the present invention.

DESCRIPTION OF THE PREFERRED EMBODIMENT

Referring to the drawing, a bearing case is generally designated by reference numeral 1, and a bearing portion generally designated by reference numeral 2, the bearing portion including tubular bearing sections 21 and 22 which may be formed of either porous material such as sintered metal or ceramics or porous synthetic resin. O-rings 3 are mounted between the bearing case 1 and the bearing portion 2. A rotatable shaft 4 for mounting thereon a cutting tool has a turbine blade 41. A cap 5 is threadably engaged with the bearing case 1. A turbine driving air supply passage 6 is provided and an air supply passage 7 for the bearing portion 2 is provided discretely from the turbine driving air supply passage 6. Sleeves 81 and 82 of inverted L-shaped or L-shaped cross section are secured to the rotatable shaft 4 in such a manner that the sleeves are in contact with the turbine blade and mounted on the outer diameter surface of the rotatable shaft 4. These sleeves 81 and 82 may be formed integrally with the rotatable shaft 4, or more advantageously manufactured separately from the shaft for convenience of working. The bearing portion 2 is formed of porous material as described above, and the section 21 of the bearing portion 2 which is adjacent a cutting tool is configured such that a clearance 91 for providing a radial air bearing is formed between the inner cylindrical surface 211 of the bearing section 21 and the outer cylindrical surface 811 of the sleeve 81. One end surface 212 of the bearing section 21 is in contact with the inner side wall 11 of the bearing case 1 and may be plated, coated with adhesive or otherwise treated to prevent leakage of air through that surface. A clearance 92 for providing a thrust air bearing is formed between the other end surface 213 of the bearing section 21 and the flanged portion 812 of the sleeve 81. In the illustrated embodiment, two O-rings 3 are mounted between the outer cylindrical surface 214 of the bearing section 21 and the inner cylindrical surface of the bearing case 1 to support bearing section 21 concentrically in the bearing case. A clearance 93 for providing a radial air bearing and a clearance 94 for providing a thrust air bearing are provided between the bearing section 22 adjacent the cap 5 and the sleeve 82, these bearings being similar to those formed 8, as between the bearing section 21 and the sleeve 81. The end surface 221 of the bearing section 22 is treated for preventing air leakage therethrough in the same manner as described with respect to the bearing section 21, and a slight clearance is formed between the end surface 221 and the cap 5. The bearing section 22 is supported concentrically in bearing case 1 by two O-rings 3.

Air supplied from an unshown compressed air supply means to the above-described device passes through the air supply passage 7 and into the two spaces defined by bearing sections 21 and 22 of the bearing portion 2, the bearing case 1 and the O-rings 3, whereafter the air flows into the bearing sections 21 and 22 through a number of pores therein and passes through the inner cylindrical surfaces of the bearing sections into the clearances 91 and 93 to form a radial air bearing. A thrust air bearing is formed primarily by the air which flows into the clearances 92 and 94 through the end surfaces of the bearing sections which are adjacent the turbine blade 41, some of the air from the radial air bearing flowing into clearances 92 and 94 to provide additional thrust bearing action. On the other hand, air supplied through the air supply passage 6 is injected against the turbine blade 41 to thereby rotate the rotatable shaft 4 with the sleeves 81 and 82. The shaft quickly assumes a high speed of rotation because it is supported by air bearings of low friction. Since the bearing portion is supported by O-rings, the damping effect provided thereby acts to absorb any vibrations occurring in the rotatable shaft during its shift from an initial rotation to high-speed rotation, thus enabling its high-speed rotation.

As compared with the dentist's handpiece using the conventional static pressure air bearing of the orifice type or the self-throttling or inherently compensated type, the device of the present invention eliminates the necessity of forming fine apertures for the orifice or the throttle, which means a greater ease and shorter time for manufacture and accordingly lower expenses of manufacture. Furthermore, the bearing of the above-mentioned conventional type is relatively small in thrust load capacity as described previously, whereas in the device of the present invention the thrust load capacity is increased because air is injected directly against the flanged portions of the sleeves 81 and 82 from the end surfaces of the bearing sections 21 and 22 in addition to the air flow from the radial bearing section. Moreover, air consumption in the device of this invention is less than that required in case of the orifice type device for supporting the same load, and an excellent cooling effect is also provided at the contacting surfaces when the rotary shaft and the bearing portion are brought into contact under a large load. It is further mentioned that in case of the orifice type device as shown, for example, in U.S. Pat. No. 3,384,344 issued to Sadayasu OTA, the member for mounting O-ring and the bearing member must be manufactured separately in order to work out the orifices in the bearing member so that in comparison to the device of this invention, the correctness and concentricity in assembling is deteriorated.

I claim:

1. A porous, static pressure air bearing device in a dentist's handpiece, said device comprising a rotatable shaft for mounting thereon a cutting tool, a bearing case, an air bearing portion provided in said bearing case for supporting said rotatable shaft, a turbine blade on said rotatable shaft, said air bearing portion being formed of a hard porous material, and radial and thrust clearances between said air bearing portion and said shaft whereby pressurized air passing through said bearing portion to said clearances provide radial and thrust bearings.

2. A bearing device according to claim 1, wherein said porous material forming said air bearing portion is sintered metal.

3. A bearing device according to claim 1, wherein said porous material forming said air bearing portion is a ceramic.

4. A bearing device according to claim 1, wherein said porous material forming said air bearing portion is a synthetic resin.

5. A bearing device according to claim 1, wherein the air bearing portion comprises a pair of spaced tubular bearing sections; and wherein the rotatable shaft has a pair of L-shaped sleeves connected thereto and related to the bearing sections to provide the radial and thrust bearing clearances.

6. A bearing device according to claim 5, wherein an O-ring is positioned between each of said bearing sections and the bearing case.

7. A bearing device according to claim 6, wherein said bearing sections are of sintered metal.

* * * * *